United States Patent [19]
Höpken et al.

[11] Patent Number: 5,945,498
[45] Date of Patent: Aug. 31, 1999

[54] POLYSILOXANE-COMPRISING PERFLUOROALKYL ETHERS AND THE PREPARATION AND USE THEREOF

[75] Inventors: Jens Höpken, Lörrach, Germany; Dieter Lohmann, Münchenstein, Switzerland; Angelika Domschke, Alpharetta, Ga.

[73] Assignee: Novartis AG, Basel, Switzerland

[21] Appl. No.: 08/776,985

[22] PCT Filed: Mar. 22, 1996

[86] PCT No.: PCT/EP96/01255

§ 371 Date: Dec. 22, 1997

§ 102(e) Date: Dec. 22, 1997

[87] PCT Pub. No.: WO96/31791

PCT Pub. Date: Oct. 10, 1996

[30] Foreign Application Priority Data

Apr. 4, 1995 [EP] European Pat. Off. ............. 95810221
May 18, 1995 [CH] Switzerland ............................ 1476/95

[51] Int. Cl.$^6$ .................................................. C08G 77/24
[52] U.S. Cl. ............................ 528/42; 526/279; 528/26; 528/28; 528/29; 528/38; 351/160 R; 264/136; 264/2.6; 523/107; 428/421; 428/447; 428/422; 623/5
[58] Field of Search ................................. 528/42, 26, 28, 528/29, 38; 526/279; 351/160 R; 264/1.36, 2.6; 523/107, 113; 428/421, 447; 623/5

[56] References Cited

U.S. PATENT DOCUMENTS

| | | | |
|---|---|---|---|
| 4,440,918 | 4/1984 | Rice | 526/246 |
| 4,818,801 | 4/1989 | Rice | 526/247 |
| 5,010,141 | 4/1991 | Mueller | 525/276 |
| 5,079,319 | 1/1992 | Mueller | 526/238 |
| 5,264,522 | 11/1993 | Mize | 524/847 |
| 5,300,613 | 4/1994 | Kishita et al. | 528/26 |
| 5,334,681 | 8/1994 | Mueller et al. | 526/243 |
| 5,380,811 | 1/1995 | Kishita et al. | 528/15 |
| 5,665,846 | 9/1997 | Sato et al. | 528/15 |
| 5,705,591 | 1/1998 | Matsuda et al. | 528/42 |

FOREIGN PATENT DOCUMENTS

| | | |
|---|---|---|
| 379462A2 | 1/1990 | European Pat. Off. . |
| 493320A2 | 12/1992 | European Pat. Off. . |
| 562878A2 | 3/1993 | European Pat. Off. . |
| 584764A1 | 8/1993 | European Pat. Off. . |
| 92247268 | 6/1992 | Japan . |

OTHER PUBLICATIONS

New Perfluoropolyether Soft Segment Containing Polyurethanes, Journal of Applied Polymer Science, vol. 57 pp. 1031–1042 (1995).

*Primary Examiner*—Margaret Glass Moore
*Attorney, Agent, or Firm*—Michael U. Lee

[57] ABSTRACT

The present invention describes a free radical polymerizable segmented macromonomer based on perfluoroelkyl ether, polysiloxane and divalent organic segments. This macromoner can be polymerized and used to form moldings, contact lenses, corneal implants and other biomedical articles.

68 Claims, No Drawings

POLYSILOXANE-COMPRISING PERFLUOROALKYL ETHERS AND THE PREPARATION AND USE THEREOF

The present invention describes a free-radical-polymerizable macromer of the formula (I) based on an unsubstituted or symmetrically substituted perfluoroalkyl ether; a polymer comprising the product of the polymerization of a novel macromer, alone or together with at least one vinylic comonomer; a process for the preparation of a macromer and a polymer; mouldings, contact lenses, corneal implants and biomedical articles made from a polymer; and articles coated with a macromer of the formula (I) or a polymerization product thereof.

Contact-lens materials having a high fluorine content and a high siloxane content are known and proven since they generally have the high oxygen permeability necessary for a contact-lens material and in addition are mostly resistant to deposits of proteins and lipids from tear fluid, and are frequently also resistant to bacterial infestation. However, the following disadvantageous properties frequently have to be accepted: loss of comfort for the contact-lens wearer owing to mechanical rigidity, reduction in oxygen permeability if the water content of the material used is relatively high, and an excessively low refractive index for good optical properties. Contact-lens materials having relatively low refractive indices are thicker than those having relatively large refractive indices and are thus also less comfortable to wear. Furthermore, suction cup effects can occur on the lenses, restricting mobility on the eye.

Japanese Patent Application 04-168 116 (JSR) describes, for example, the preparation of oxygen-permeable polymers comprising the product of the copolymerization of, for example, methyl methacrylate with a macromer built up from a perfluoroalkyl ether, which may be bonded at each end to an unsaturated polymerizable group via one or more siloxanyl units and a plurality of bivalent hydrocarbon radicals. It is stated that these polymers can be used as ophthalmic material.

EP 0 379 462 describes ethylenically substituted macromers which contain perfluoroalkyl ether and polyalkyl ether segments and are used for the production of polymers and ophthalmic devices, such as intraocular implants and contact lenses, and furthermore crosslinked polymers with vinyl monomers.

It has been found that a novel and balanced composition gives a macromer which can be polymerized, if desired together with at least one vinylic comonomer (a), to give a material which is substantially free from the undesired properties indicated above.

The present invention relates to a macromer of the formula (I)

$$P_1-(Y)_m-(L-X_1)_p-Q-(X_1-L)_p-(Y)_m-P_1 \qquad (I)$$

where each $P_1$, independently of the others, is a free-radical-polymerizable group; each Y, independently of the others, is —CONHCOO—, —CONHCONH—, —OCONHCO—, —NHCONHCO—, —NHCO—, —CONH—, —NHCONH—, —COO—, —OCO—, —NHCOO— or —OCONH—; m and p, independently of one another, are 0 or 1; each L, independently of the others, is a divalent radical of an organic compound having up to 20 carbon atoms; each $X_1$, independently of the others, is —NHCO—, —CONH—, —NHCONH—, —COO—, —OCO—, —NHCOO— or —OCONH—; and Q is a bivalent polymer fragment consisting of the segments (a) —$(E)_k$—Z—$CF_2$—$(OCF_2)_x$—$(OCF_2CF_2)_y$—$OCF_2$—Z—$(E)_k$—, where x+y is a number in the range from 10 to 30; each Z, independently of the others, is a divalent radical having up to 12 carbon atoms or a bond; each E, independently of the others, is —$(OCH_2CH_2)_q$—, where q has a value of from 0 to 2, and where the link —Z—E— represents the sequence —Z—$(OCH_2CH_2)_q$—; and k is 0 or 1;

(b)

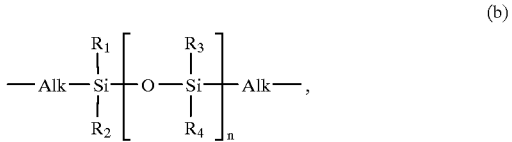

where n is an integer from 5 to 100; Alk is alkylene having up to 20 carbon atoms; 80–100% of the radicals $R_1$, $R_2$, $R_3$ and $R_4$, independently of one another, are alkyl and 0–20% of the radicals $R_1$, $R_2$, $R_3$ and $R_4$, independently of one another, are alkenyl, aryl or cyanoalkyl; and (c) $X_2$—R—$X_2$, where R is a divalent organic radical having up to 20 carbon atoms, and each $X_2$, independently of the others, is —NHCO—, —CONH—, —NHCONH—, —COO—, —OCO—, —NHCOO— or —OCONH—;

with the proviso that each segment (a) or (b) has a segment (c) attached to it; and each segment (c) has a segment (a) or (b) attached to it.

The number of segments (b) in the polymer fragment Q is preferably greater than or equal to the number of segments (a).

The ratio between the number of segments (a) and (b) in the polymer fragment Q is preferably 3:4, 2:3, 1:2 or 1:1.

The molar ratio between the number of segments (a) and (b) in the polymer fragment Q is more preferably 2:3, 1:2 or 1:1.

The mean molecular weight of the polymer fragment Q is in the range from about 1000 to about 20,000, preferably in the range from about 3000 to about 15,000, particularly preferably in the range from about 5000 to about 12,000.

The total number of segments (a) and (b) in the polymer fragment Q is preferably in the range from 2 to about 11, particularly preferably in the range from 2 to about 9, and in particular in the range from 2 to about 7. The smallest polymer unit Q is preferably composed of one perfluoro segment (a), one siloxane segment (b) and one segment (c).

In a preferred embodiment of the polymer fragment Q, which preferably has a composition in the abovementioned ratios, the polymer fragment Q is terminated at each end by a siloxane segment (b).

In another preferred embodiment of the polymer fragment Q, which preferably has a composition in the abovementioned ratios, the polymer fragment Q is terminated at one end by a perfluoro segment (a) and at the other end by a siloxane segment (b).

Said compositions in a bivalent polymer fragment Q always correspond above and below to a mean statistical composition. This means that, for example, even individual block copolymer radicals containing identical recurring units are included, so long as the final mean statistical composition is as specified.

$X_1$ is preferably —NHCONH—, —NHCOO— or —OCONH—, particularly preferably —NHCOO— or —OCONH—.

The $X_2$—R—$X_2$ segment is preferably a radical derived from a diisocyanate, where each $X_2$, independently of the other, is —NHCONH—, —NHCOO— or —OCONH—, in particular —NHCOO— or —OCONH—.

Z is preferably a bond, lower alkylene or —CONH-arylene, in which the —CO— moiety is linked to a $CF_2$ group. Z is particularly preferably lower alkylene, in particular methylene.

q is preferably 0, 1, 1.5 or 2, particularly preferably 0 or 1.5.

The perfluoroalkoxy units $OCF_2$ and $OCF_2CF_2$ with the indices x and y in segment (a) can either have a random distribution or be in the form of blocks in a chain. The sum of the indices x+y is preferably a number in the range from 10 to 25, particularly preferably from 10 to 15. The ratio x:y is preferably in the range from 0.5 to 1.5, in particular in the range from 0.7 to 1.1.

A free-radical-polymerizable group $P_1$ is, for example, alkenyl, alkenylaryl or alkenylarylenealkyl having up to 20 carbon atoms. Examples of alkenyl are vinyl, allyl, 1-propen-2-yl, 1-buten-2-, -3- and -4-yl, 2-buten-3-yl, and the isomers of pentenyl, hexenyl, octenyl, decenyl and undecenyl. Examples of alkenylaryl are vinylphenyl, vinylnaphthyl or allylphenyl. An example of alkenylarylenealkyl is o-, m-, or p-vinylbenzyl.

$P_1$ is preferably alkenyl or alkenylaryl having up to 12 carbon atoms, particularly preferably alkenyl having up to 8 carbon atoms, in particular alkenyl having up to 4 carbon atoms.

Y is preferably —COO—, —OCO—, —NHCONH—, —NHCOO—, —OCONH—, —NHCO— or —CONH—, particularly preferably —COO—, —OCO—, —NHCO— or —CONH— in particular —COO— or —OCO—.

In a preferred embodiment, the indices m and p are not simultaneously zero. If p is zero, m is preferably 1.

L is preferably alkylene, arylene, a saturated bivalent cycloaliphatic group having 6 to 20 carbon atoms, arylenealkylene, alkylenearylene, alkylenearylenealkylene or arylenealkylenearylene.

In a preferred meaning, L is a divalent radical having up to 12 carbon atoms, particularly preferably a divalent radical having up to 8 carbon atoms. In a preferred meaning, L is furthermore alkylene or arylene having up to 12 carbon atoms. A particularly preferred meaning of L is lower alkylene, in particular lower alkylene having up to 4 carbon atoms.

The divalent radical R is, for example, alkylene, arylene, alkylenearylene, arylenealkylene or arylenealkylenearylene having up to 20 carbon atoms, a saturated bivalent cycloaliphatic group having 6 to 20 carbon atoms or cycloalkylenealkylenecycloalkylene having 7 to 20 carbon atoms.

In a preferred meaning, R is alkylene, arylene, alkylenearylene, arylenealkylene or arylenealkylenearylene having up to 14 carbon atoms or a saturated divalent cycloaliphatic group having 6 to 14 carbon atoms.

In a preferred meaning, R is alkylene, arylene, alkylenearylene or arylenealkylene having up to 14 carbon atoms or a saturated divalent cycloaliphatic group having 6 to 14 carbon atoms.

In a preferred meaning, R is alkylene or arylene having up to 12 carbon atoms or a saturated bivalent cycloaliphatic group having 6 to 14 carbon atoms.

In a preferred meaning, R is alkylene or arylene having up to 10 carbon atoms or a saturated bivalent cycloaliphatic group having 6 to 10 carbon atoms.

In a particularly preferred meaning, R is a radical derived from a diisocyanate, for example from hexane 1,6-diisocyanate, 2,2,4-trimethylhexane 1,6-diisocyanate, tetramethylene diisocyanate, phenylene 1,4-diisocyanate, toluene 2,4-diisocyanate, toluene 2,6-diisocyanate, m- or p-xylene diisocyanate, isophorone diisocyanate or cyclohexane 1,4-diisocyanate.

In a preferred meaning, n is an integer from 5 to 70, particularly preferably 10 to 50, in particular 14 to 28.

In a preferred meaning, 80–100%, preferably 85–100%, in particular 90–100%, of the radicals $R_1$, $R_2$, $R_3$ and $R_4$ are, independently of one another, lower alkyl having up to 8 carbon atoms, particularly preferably lower alkyl having up to 4 carbon atoms, especially lower alkyl having up to 2 carbon atoms. A further particularly preferred meaning of $R_1$, $R_2$, $R_3$ and $R_4$ is methyl.

In a preferred meaning, 0–20%, preferably 0–15%, in particular 0–10%, of the radicals $R_1$, $R_2$, $R_3$ and $R_4$ are, independently of one another, lower alkenyl, unsubstituted or lower alkyl- or lower alkoxy-substituted phenyl or cyano (lower alkyl).

Arylene is preferably phenylene or naphthylene, which is unsubstituted or substituted by lower alkyl or lower alkoxy, in particular 1,3-phenylene, 1,4-phenylene or methyl-1,4-phenylene, 1,5-naphthylene or 1,8-naphthylene.

Aryl is a carbocyclic aromatic radical which is unsubstituted or substituted preferably by lower alkyl or lower alkoxy. Examples are phenyl, tolyl, xylyl, methoxyphenyl, t-butoxyphenyl, naphthyl and phenanthryl.

A saturated bivalent cycloaliphatic group is preferably cycloalkylene, for example cyclohexylene or cyclohexylene (lower alkylene), for example cyclohexylenemethylene, which is unsubstituted or substituted by one or more lower alkyl groups, for example methyl groups, for example trimethylcyclohexylenemethylene, for example the bivalent isophorone radical.

For the purposes of the present invention, the term "lower" in connection with radicals and compounds, unless defined otherwise, denotes, in particular, radicals or compounds having up to 8 carbon atoms, preferably having up to 4 carbon atoms.

Lower alkyl has, in particular, up to 8 carbon atoms, preferably up to 4 carbon atoms, and is, for example, methyl, ethyl, propyl, butyl, tert-butyl, pentyl, hexyl or isohexyl.

Alkylene has up to 12 carbon atoms and can be straight-chain or branched. Suitable examples are decylene, octylene, hexylene, pentylene, butylene, propylene, ethylene, methylene, 2-propylene, 2-butylene and 3-pentylene.

Lower alkylene is alkylene having up to 8 carbon atoms, particularly preferably up to 4 carbon atoms. Particularly preferred meanings of lower alkylene are propylene, ethylene and methylene.

The arylene unit in alkylenearylene or arylenealkylene is preferably phenylene, unsubstituted or substituted by lower alkyl or lower alkoxy, and the alkylene unit therein is preferably lower alkylene, such as methylene or ethylene, in particular methylene. These radicals are therefore preferably phenylenemethylene or methylenephenylene.

Lower alkoxy has, in particular, up to 8 carbon atoms, preferably up to 4 carbon atoms, and is, for example, methoxy, ethoxy, propoxy, butoxy, tert-butoxy or hexyloxy.

Arylenealkylenearylene is preferably phenylene(lower alkylene)phenylene having up to 8, in particular up to 4, carbon atoms in the alkylene unit, for example phenyleneethylenephenylene or phenylenemethylenephenylene.

A preferred embodiment is a macromer according to formula (I) wherein $P_1$ is independently of the other lower alkenyl, Y is independently of the other —COO— or —OCO—, L is independently of the other lower alkylene, $X_1$ is independently of the other —NHCOO— or —OCONH—, p and m are 1; the polymer fragment Q has up to 3 segments (a), up to 4 segments (b) and up to 6 segments (c), wherein in segment (a) the sum of the indices x+y is in the range of 10–15, Z is lower alkylene and k is 0, wherein in segment (b) Alk is lower alkylene, the radicals $R_1$, $R_2$, $R_3$ and $R_4$ are each independently of the others lower alkyl and n is in the range of 14–28, and wherein in segment (c) R is alkylene or arylene having up to 14 carbon atoms or a saturated divalent cycloaliphatic group having 6–14 carbon atoms, and $X_2$ is —NHCOO— or —OCONH—.

Another preferred embodiment is a macromer according to formula (I) wherein $P_1$ is independently of the other lower alkenyl, Y is independently of the other —COO— or —OCO—, L is independently of the other lower alkylene, $X_1$ is independently of the other —NHCOO— or —OCONH—, p and m are 1; the polymer fragment Q has one segment (a), up to 2 segments (b) and up to 2 segments (c), wherein in segment (a) the sum of the indices x+y is in the range of 10–15, Z is lower alkylene and k is 0, wherein in segment (b) Alk is lower alkylene, the radicals $R_1$, $R_2$, $R_3$ and $R_4$ are each independently of the others lower alkyl and n is in the range of 14–28, and wherein in segment (c) R is alkylene or arylene having up to 14 carbon atoms or a saturated divalent cycloaliphatic group having 6–14 carbon atoms, and $X_2$ is —NHCOO— or —OCONH—.

Another preferred embodiment is a macromer according to formula (I) wherein $P_1$ is independently of the other alkenyl having up to 4 carbon atoms, Y is independently of the other —COO— or —OCO—, L is independently of the other lower alkylene, $X_1$ is independently of the other —NHCOO— or —OCONH—, p and m are 1; the polymer fragment Q has one segment (a), 2 segments (b) 2 segments (c), wherein in segment (a) the sum of the indices x+y is in the range of 10–15, Z is lower alkylene and k is 0, wherein in segment (b) Alk is lower alkylene, the radicals $R_1$, $R_2$, $R_3$ and $R_4$ are each independently of the others lower alkyl and n is in the range of 14–28, and wherein in segment (c) R is alkylene or arylene having up to 14 carbon atoms or a saturated divalent cycloaliphatic group having 6–14 carbon atoms, and $X_2$ is —NHCOO— or —OCONH—.

Another preferred embodiment is a macromer according to formula (I) wherein $P_1$ is independently of the other lower alkenyl, Y is independently of the other —COO— or —OCO—, L is independently of the other lower alkylene, $X_1$ is independently of the other —NHCOO— or —OCONH—, p and m are 1; the polymer fragment Q has one segment (a), up to 2 segments (b) and up to 2 segments (c), wherein in segment (a) the sum of the indices x+y is in the range of 10–15, Z is lower alkylene and k is 0, wherein in segment (b) Alk is lower alkylene, the radicals $R_1$, $R_2$, $R_3$ and $R_4$ are each methyl and n is in the range of 14–28, and wherein in segment (c) R is alkylene or arylene having up to 14 carbon atoms or a saturated divalent cycloaliphatic group having 6–14 carbon atoms, and $X_2$ is —NHCOO— or —OCONH—.

Another preferred embodiment is a macromer according to formula (I) wherein $P_1$ is independently of the other lower alkenyl having up to 4 C-atoms, Y is independently of the other —COO— or —OCO—, L is independently of the other lower alkylene having up to 4 carbon atoms, $X_1$ is independently of the other —NHCOO— or —OCONH—, p and m are 1; the polymer fragment Q has one segment (a), up to 2 segments (b) and up to 2 segments (c), wherein in segment (a) the sum of the indices x+y is in the range of 10–15, Z is lower alkylene and k is 0, wherein in segment (b) Alk is lower alkylene having up to 4 carbon atoms, the radicals $R_1$, $R_2$, $R_3$ and $R_4$ are each independently of the others lower alkyl having up to 4 carbon atoms and n is in the range of 14–28, and wherein in segment (c) R is a saturated divalent cycloaliphatic group having 6–14 carbon atoms, and $X_2$ is —NHCOO— or —OCONH—.

The macromers of the formula (I) can be prepared by processes known per se, for example as follows:

In a first step, a perfluoropolyalkyl ether derivative of the formula (IV)

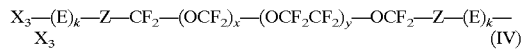
(IV)

in which $X_3$ is —OH, —$NH_2$, —COOH, —COCl, —NCO or —$COOR_5$, where —$COOR_5$ is generally an activated ester in which $R_5$ is alkyl or aryl which is unsubstituted or substituted by halogen or cyano, and the variables Z, E, k, x and y are as defined above, is preferably reacted with two equivalents of a bifunctional radical of the formula (V)

(V)

in which R is as defined above and $X_4$ is a functional radical which is coreactive with an $X_3$ and is preferably —OH—, —$NH_2$, —COOH, —COCl, —$COOR_5$ or —NCO, in the presence or absence of a suitable catalyst, where the reaction of $X_3$ with $X_4$ gives a group $X_2$; after which a reactive derivative of the formula (VI)

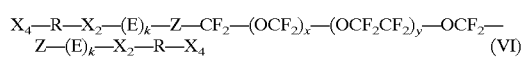
(VI)

is obtained which is then preferably reacted with two equivalents of an α,ω-substituted siloxane of the formula (VII)

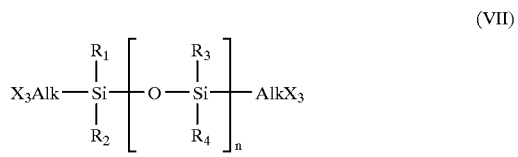
(VII)

where the variables $R_1$, $R_2$, $R_3$, $R_4$, n, $X_3$ and Alk are as defined above, in the presence or absence of a suitable catalyst, giving a compound of the formula (VIII)

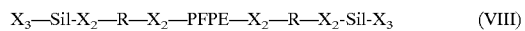
(VIII)

in which PFPE is $(E)_k$—Z—$CF_2$—$(OCF_2)_x$—$(OCF_2CF_2)_y$—$OCF_2$—Z—$(E)_k$, Sil is the siloxane radical

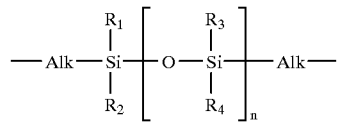

and the other variables are as defined above; after which the reactive intermediate of the formula (VIII) is preferably reacted with two equivalents of a compound of the formula (IXa) or (IXb)

(IXa)

(IXb)

in the presence or absence of a catalyst, to give the macromer of the formula (I)

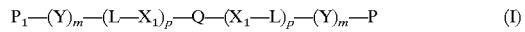
(I)

in which $Y_2$ is a functional radical which is coreactive with $X_3$ and is preferably —OH, —$NH_2$, —COOH, —COCl, —COOR$_5$, —CONCO or —NCO, and the variables are as defined above, and in which X$_1$ is formed from the reaction of X$_3$ with X$_4$ and Y is formed from the reaction of Y$_2$ with X$_3$.

The starting materials of the formula (IV) for the preparation of the perfluoroalkyl ethers are known and many are commercially available. For example, U.S. Pat. No. 3,810, 875 and EP 0 211 237 also describe such compounds. Ausimont, Italy, markets perfluoroalkyl ether dimethanols under the name Fomblin, for example Fomblin ZDOL and Fomblin ZDOL-TX. Further Fomblin derivatives of the formula (IV) are commercially available and are, for example, Fomblin Z DISOC, in which the radical —Z—X$_3$ in the formula (IV) is —CONH—C$_6$H$_3$(CH$_3$)—NCO, Fomblin Z DEAL, in which the radical —Z—X$_3$ in the formula (IV) is —COOR$_5$, and Fomblin Z DIAC, in which the radical —Z—X$_3$ in the formula (IV) is —COOH.

Bifunctional radicals having a substitution pattern as per formula (V) exist in large numbers and are commercially available. Examples which may be mentioned are: diisocyanates, for example isophorone diisocyanate and 2,2,4-trimethylhexane 1,6-diisocyanate; diols, for example glycol and cyclohexane-1,2-diol; dicarboxylic acids, for example adipic acid and maleic acid; diamines, for example ethylenediamine and hexamethylenediamine, diesters, for example diethyl phthalate and dibutyl malonate; derivatives containing various functional groups, for example 2-aminoethanol, monomethyl malonate, glycolic acid, salicylic acid, glycine and glycine methyl ester.

Preferance is given to bifunctional derivatives of the formula (V) which have different reactivities irrespective of the nature of their functional radicals X$_4$. In the case of identical radicals X$_4$, this is achieved, for example, through different steric requirements in the direct vicinity of a radical X$_4$. Examples thereof are isophorone diisocyanate, 2,2,4-trimethylhexane 1,6-diisocyanate and toluene 2,4-diisocyanate. The advantage of using bifunctional derivatives of the formula (V) of different reactivity is that the chain length of the polymer Q (number of segments (a), (b) and (c)) is easily adjustable and controllable.

α,ω-substituted siloxanes of the formula (VII) are likewise commercially available, for example α,ω-hydroxypropyl-terminated polydimethylsiloxane KF6001 from Shin-Etsu.

The novel compounds can be prepared in the presence or absence of a solvent. It is advantageous to use a substantially inert solvent, ie. one which does not participate in the reaction. Suitable examples thereof are ethers, such as tetrahydrofuran (THF), diethyl ether, diethylene glycol dimethyl ether or dioxane, halogenated hydrocarbons, such as chloroform or methylene chloride, bipolar aprotic solvents, such as acetonitrile, acetone, dimethylformamide (DMF) or dimethyl sulfoxide (DMSO), hydrocarbons, such as hexane, petroleum ether, toluene or xylene, and furthermore pyridine or N-methylmorpholine.

In the preparation of novel compounds, the reactants are advantageously employed in stoichiometric amounts. The reaction temperature can be, for example, from −30° C. to 150° C., preferably from 0° to room temperature. The reaction times are in the range from about 15 minutes to 7 days, preferably in the region of about 12 hours. If necessary, the reaction is carried out under argon or nitrogen as protective gas. In urethane-forming reactions, a suitable catalyst, for example dibutyltin dilaurate (DBTDL), is advantageously added.

The present invention furthermore relates to a polymer comprising a product of the polymerization of at least one compound of the formula (I) as defined above and, if desired, at least one vinylic comonomer (a).

In the preferred composition of a novel copolymer, the proportion by weight of a compound of the formula (I) is in the range from 100 to 0.5%, in particular in the range from 80 to 10%, preferably in the range from 70 to 30%, based on the total polymer.

In a preferred polymer comprising a product of the polymerization of at least one compound of the formula (I), comonomer (a) is absent and the polymer is a homopolymer.

A comonomer (a) present in the novel polymer can be hydrophilic or hydrophobic or a mixture thereof. Suitable comonomers are, in particular, those which are usually used in the production of contact lenses and biomedical materials.

A hydrophobic comonomer (a) is taken to mean a monomer which typically gives a homopolymer which is insoluble in water and can absorb less than 10% by weight of water.

Analogously, a hydrophilic comonomer (a) is taken to mean a monomer which typically gives a homopolymer which is soluble in water or can absorb at least 10% by weight of water.

Suitable hydrophobic comonomers (a) are, without this being an exhaustive list, $C_1$–$C_{18}$alkyl and $C_3$–$C_{18}$cycloalkyl acrylates and methacrylates, $C_3$–$C_{18}$alkylacrylamides and -methacrylamides, acrylonitrile, methacrylonitrile, vinyl $C_1$–$C_{18}$alkanoates, $C_2$–$C_{18}$alkenes, $C_2$–$C_{18}$haloalkenes, styrene, (lower alkyl)styrene, lower alkyl vinyl ethers, $C_2$–$C_{10}$perfluoroalkyl acrylates and methacrylates and correspondingly partially fluorinated acrylates and methacrylates, $C_3$–$C_{12}$perfluoroalkylethylthiocarbonylaminoethyl acrylates and methacrylates, acryloxy- and methacryloxyalkylsiloxanes, N-vinylcarbazole, $C_1$–$C_{12}$alkyl esters of maleic acid, fumaric acid, itaconic acid, mesaconic acid and the like. Preference is given, for example, to acrylonitrile, $C_1$–$C_4$alkyl esters of vinylically unsaturated carboxylic acids having 3 to 5 carbon atoms or vinyl esters of carboxylic acids having up to 5 carbon atoms.

Examples of suitable hydrophobic comonomers (a) are methyl acrylate, ethyl acrylate, propyl acrylate, isopropyl acrylate, cyclohexyl acrylate, 2-ethylhexyl acrylate, methyl methacrylate, ethyl methacrylate, propyl methacrylate, butyl acrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyltoluene, vinyl ethyl ether, perfluorohexylethylthiocarbonylaminoethyl methacrylate, isobornyl methacrylate, trifluoroethyl methacrylate, hexafluoroisopropyl methacrylate, hexafluorobutyl methacrylate, tristrimethylsilyloxysilylpropyl methacrylate (TRIS), 3-methacryloxypropylpentamethyldisiloxane and bis (methacryloxypropyl)tetramethyldisiloxane.

Preferred examples of hydrophobic comonomers (a) are methyl methacrylate, TRIS and acrylonitrile.

Suitable hydrophilic comonomers (a) are, without this being an exhaustive list, hydroxyl-substituted lower alkyl acrylates and methacrylates, acrylamide, methacrylamide, (lower alkyl)acrylamides and -methacrylamides, ethoxylated acrylates and methacrylates, hydroxyl-substituted (lower alkyl)acrylamides and -methacrylamides, hydroxyl-substituted lower alkyl vinyl ethers, sodium vinylsulfonate, sodium styrenesulfonate, 2-acrylamido-2-methylpropanesulfonic acid, N-vinylpyrrole, N-vinyl-2-pyrrolidone, 2-vinyloxazoline, 2-vinyl-4,4'-dialkyloxazolin-5-one, 2- and 4-vinylpyridine, vinylically unsaturated carboxylic acids having a total of 3 to 5 carbon atoms, amino(lower alkyl)- (where the term "amino" also includes quaternary ammonium), mono(lower alkylamino)(lower alkyl) and di(lower alkylamino)(lower alkyl) acrylates and methacrylates, allyl alcohol and the like. Preference is given, for example, to N-vinyl-2-pyrrolidone, acrylamide, methacrylamide, hydroxyl-substituted lower alkyl acrylates and methacrylates, hydroxy-substituted (lower alkyl) acrylamides and -methacrylamides and vinylically unsaturated carboxylic acids having a total of 3 to 5 carbon atoms.

Examples of suitable hydrophilic comonomers (a) are hydroxyethyl methacrylate (HEMA), hydroxyethyl acrylate, hydroxypropyl acrylate, trimethylammonium 2-hydroxypropylmethacrylate hydrochloride (Blemer® QA, for example from Nippon Oil), dimethylaminoethyl methacrylate (DMAEMA), dimethylaminoethylmethacrylamide, acrylamide, methacrylamide, N,N-dimethylacrylamide (DMA), allyl alcohol, vinylpyridine, glycerol methacrylate, N-(1,1-dimethyl-3-oxobutyl)acrylamide, N-vinyl-2-pyrrolidone (NVP), acrylic acid, methacrylic acid and the like.

Preferred hydrophilic comonomers (a) are 2-hydroxyethyl methacrylate, dimethylaminoethyl methacrylate, trimethylammonium 2-hydroxypropylmethacrylate hydrochloride, N,N-dimethylacrylamide and N-vinyl-2-pyrrolidone.

The novel polymers are synthesized in a manner known per se from the corresponding monomers (the term monomer here also including a macromer according to the definition of the formula (I)) by a polymerization reaction customary to the person skilled in the art. Usually, a mixture of the abovementioned monomers is warmed with addition of a free-radical former. Examples of such free-radical formers are azodiisobutyronitrile (AIBN), potassium peroxodisulfate, dibenzoyl peroxide, hydrogen peroxide and sodium percarbonate. If, for example, said compounds are warmed, free radicals form with homolysis, and can then initiate, for example, a polymerization.

A polymerization reaction can particularly preferably be carried out using a photoinitiator. In this case, the term photopolymerization is used. In the photopolymerization, it is appropriate to add a photoinitiator which can initiate free-radical polymerization and/or crosslinking by using light. Examples thereof are customary to the person skilled in the art; suitable photoinitiators are, in particular, benzoin methyl ether, 1-hydroxycyclohexylphenyl ketone, Darocur and Irgacur products, preferably Darocur 1173® and Irgacur 2959®. Also suitable are reactive photoinitiators, which can be incorporated, for example, into a macromer, or can be used as a specific comonomer (a). Examples thereof are given in EP 0 632 329. The photopolymerization can then be initiated by actinic radiation, for example light, in particular UV light having a suitable wavelength. The spectral requirements can, if necessary, be controlled appropriately by addition of suitable photosensitizers.

A polymerization can be carried out in the presence or absence of a solvent. Suitable solvents are in principle all solvents which dissolve the monomers used, for example water, alcohols, such as lower alkanols, for example ethanol or methanol, furthermore carboxamides, such as dimethylformamide, dipolar aprotic solvents, such as dimethyl sulfoxide or methyl ethyl ketone, ketones, for example acetone or cyclohexanone, hydrocarbons, for example toluene, ethers, for example THF, dimethoxyethane or dioxane, halogenated hydrocarbons, for example trichloroethane, and also mixtures of suitable solvents, for example mixtures of water and an alcohol, for example a water/ethanol or water/methanol mixture.

A polymer network can, if desired, be reinforced by addition of a crosslinking agent, for example a polyunsaturated comonomer (b). In this case, the term crosslinked polymers is preferably used.

The invention therefore furthermore relates to a crosslinked polymer comprising the product of the polymerization of a macromer of the formula (I), if desired with at least one vinylic comonomer (a) and with at least one polyunsaturated comonomer (b).

Examples of typical polyunsaturated comonomers (b) are allyl (meth)acrylate, lower alkylene glycol di(meth)acrylate, poly(lower alkylene) glycol di(meth)acrylate, lower alkylene di(meth)acrylate, divinyl ether, divinyl sulfone, di- and trivinylbenzene, trimethylolpropane tri(meth)acrylate, pentaerythritol tetra(meth)acrylate, bisphenol A di(meth) acrylate, methylenebis(meth)acrylamide, triallyl phthalate and diallyl phthalate.

The amount of the polyunsaturated comonomer (b) used is expressed in a proportion by weight based on the total polymer and is in the range from 20 to 0.05%, in particular in the range from 10 to 0.1%, preferably in the range from 2 to 0.1%.

A preferred embodiment relates also to a polymer which comprises the polymerization product of the following components in weight percent based on the total weight of the polymer:

(1) 45–65% of a macromer according to the main claim,
(2) 15–30% of a hydrophobic monomer, and
(3) 10–35% of a hydrophilic monomer.

Another preferred embodiment relates also to a polymer which comprises the polymerization product of the following components in weight percent based on the total weight of the polymer:

(1) 45–65% of a macromer according to formula (I) wherein $P_1$ is independently of the other lower alkenyl, Y is independently of the other —COO— or —OCO—, L is independently of the other lower alkylene, $X_1$ is independently of the other —NHCOO— or —OCONH—, p and m are 1; the polymer fragment Q has up to 3 segments (a), up to 4 segments (b) and up to 6 segments (c), wherein in segment (a) the sum of the indices x+y is in the range of 10–15, Z is lower alkylene and k is 0, wherein in segment (b) Alk is lower alkylene, the radicals $R_1$, $R_2$, $R_3$ and $R_4$ are each independently of the others lower alkyl and n is in the range of 14–28, and wherein in segment (c) R is alkylene or arylene having up to 14 carbon atoms or a saturated divalent cycloaliphatic group having 6–14 carbon atoms, and $X_2$ is —NHCOO— or —OCONH—, (2) 15–30% of a hydrophobic monomer, and
(3) 10–35% of a hydrophilic monomer.

Another preferred embodiment relates also to a polymer which comprises the polymerization product of the following components in weight percent based on the total weight of the polymer:

(1) 45–65% of a macromer according to formula (I) wherein $P_1$ is independently of the other lower alkenyl having up to 4 C-atoms, Y is independently of the other —COO— or —OCO—, L is independently of the other lower alkylene having up to 4 carbon atoms, $X_1$ is independently of the other —NHCOO— or —OCONH—, p and m are 1; the polymer fragment Q has one segment (a), up to 2 segments (b) and up to 2 segments (c), wherein in segment (a) the sum of the indices x+y is in the range of 10–15, Z is lower alkylene and k is 0, wherein in segment (b) Alk is lower alkylene having up to 4 carbon atoms, the radicals $R_1$, $R_2$, $R_3$ and $R_4$ are each independently of the others lower alkyl having up to 4 carbon atoms and n is in the range of 14–28, and wherein in segment (c) R is a saturated divalent cycloaliphatic group having 6–14 carbon atoms, and $X_2$ is —NHCOO— or —OCONH—, (2) 15–30% of a hydrophobic monomer, and (3) 10–35% of a hydrophilic monomer.

Another preferred embodiment relates to a polymer which comprises the polymerization product of the following components in weight percent based on the total weight of the polymer:

(1) 50–60% of a macromer according to the main claim, (2) 20–25% of a hydrophobic monomer, and (3) 15–30% of a hydrophilic monomer.

Another preferred embodiment relates to a polymer which comprises the polymerization product of the following components in weight percent based on the total weight of the polymer:

(1) 50–60% of a macromer of formula (I) according to the definition in the main claim, wherein $P_1$ is independently of the other lower alkenyl, Y is independently of the other —COO— or —OCO—, L is independently of the other lower alkylene, $X_1$ is independently of the other —NHCOO— or —OCONH—, p and m are 1; the polymer fragment Q has up to 3 segments (a), up to 4 segments (b) and up to 6 segments (c), wherein in segment (a) the sum of the indices x+y is in the range of 10–15, Z is lower alkylene and k is 0, wherein in segment (b) Alk is lower alkylene, the radicals $R_1$, $R_2$, $R_3$ and $R_4$ are each independently of the others lower alkyl and n is in the range of 14–28, and wherein in segment (c) R is alkylene or arylene having up to 14 carbon atoms or a saturated divalent cycloaliphatic group having 6–14 carbon atoms, and $X_2$ is —NHCOO— or —OCONH—, (2) 20–25% of a hydrophobic monomer, and (3) 15–30% of a hydrophilic monomer.

Another preferred embodiment relates to a polymer which comprises the polymerization product of the following components in weight percent based on the total weight of the polymer:

(1) 50–60% of a macromer according to the main claim, (2) 20–25% of a hydrophobic monomer, (3) 15–30% of a hydrophilic monomer, and (4) 0.1–2% of a polyunsaturated comonomer (b).

The novel polymers or crosslinked polymers can be converted into mouldings in a manner known per se, in particular into contact lenses, for example by carrying out the photopolymerization or photocrosslinking of the novel polymers in a suitable contact-lens mould. The invention therefore furthermore relates to mouldings essentially comprising novel polymers or crosslinked polymers. Further examples of novel mouldings, in addition to contact lenses, are biomedical articles or in particular ophthalmic mouldings, for example artifical corneas, intraocular lenses, eye bandages, mouldings used in surgery, such as heart valves, artifical arteries or the like, furthermore coatings, films or membranes, for example membranes for diffusion control, photostructurable films for information storage, or photoresist materials, for example membranes or mouldings for etch resists or screen printing resists, furthermore particles, in particular microparticles, capsules, in particular microcapsules, films and plasters for drug delivery systems.

A specific embodiment of the invention is directed to contact lenses which essentially comprise or consist of a novel polymer or polymeric network. Such contact lenses have a range of unusual and extremely advantageous properties. Amongst these properties are, for example, their excellent compatibility with the human cornea and with tear fluid, if necessary after suitable surface treatment (e.g. coating), which is based on a balanced ratio between water content, oxygen permeability and mechanical and adsorptive properties. This results in high comfort and the absence of irritation and allergenic effects. Owing to their favourable permeability properties with respect to various salts, nutrients, water and diverse other components of tear fluid and gases ($CO_2$ and $O_2$), the novel contact lenses have no effect, or virtually no effect, on the natural metabolic processes in the cornea. In contrast to many other siloxane-containing contact lenses, hydrophilic lenses, for example, which contain the macromer of the formula (I) as essential constituent do not have the undesired suction cup effect. Furthermore, the novel contact lenses have high dimensional stability and shelf life.

Surface treatment as is referred to above, in particular refers to a process to render a surface ophthalmically more compatible, in which, by means of contact with a vapor or liquid, and/or by means of application of an energy source (a) a coating is applied to the surface to an article, (b) chemical species are adsorbed onto the surface of an article, (c) the chemical nature (e.g. electrostatic charge) of chemical groups on the surface of an article are altered, or (d) the surface properties of an article are otherwise modified.

There are a variety of methods disclosed in the art for rendering a surface of a material hydrophilic. For example, the lens may be coated with a layer of a hydrophilic polymeric material. Alternatively, hydrophilic groups may be grafted onto the surface of the lens, thereby producing a monolayer of hydrophilic material. These coating or grafting processes may be effected by a number of processes, including without limitation thereto, exposing the lens to plasma gas or immersing the lens in a monomeric solution under appropriate conditions.

Another set of methods of altering the surface properties of a lens involves treatment prior to polymerization to form the lens. For example, the mold may be treated with plasma (i.e. an ionized gas), a static electrical charge, irradiation, or other energy source, thereby causing the prepolymerization mixture immediately adjacent the mold surface to differ in composition from the core of the prepolymerization mixture.

A preferred class of surface treatment processes are plasma processes, in which an ionized gas is applied to the surface of an article. Plasma gases and processing conditions are described more fully in U.S. Pat. No. 4,312,575 and U.S. Pat. No. 4,632,844, which are incorporated herein by reference. The plasma gas is preferably a mixture of lower alkanes and nitrogen, oxygen or an inert gas.

In a preferred embodiment, the lens is plasma treated in the presence of a mixture of (a) a $C_1$–$C_6$alkane and (b) a gas selected from the group consisting of nitrogen, argon, oxygen, and mixtures thereof. A $C_1$–$C_6$alkane (a) is preferably selected from a $C_1$–$C_4$alkane and may for example be methane, propane or butane. A gas (b) is preferably selected from nitrogen, oxygen and a mixture thereof and in particular from air, wherein air within the meaning of the present invention denotes 79% nitrogen and 21% oxygen. In a more preferred embodiment, the lens is plasma treated in the presence of a mixture of methane and air. The plasma treatment (apparatus and process) as is referred to herein is preferably carried out in analogy to the disclosure of H. Yasuda, "Plasma Polymerization", Academic Press, Orlando, Fla. (1985), pages 319 forward.

The present invention also relates to a moulding comprising one of the novel polymers, wherein the surface of the moulding is plasma treated in the presence of a $C_1$–$C_6$alkane (a) and a gas (b) which is selected from the group consisting of nitrogen, argon, oxygen, and mixtures thereof.

A preferred embodiment relates to a moulding which comprises the polymer of a polymerization product of the following components in weight percent based on the total weight of the polymer.

(1) 45–65% of a macromer according to formula (I) wherein $P_1$ is independently of the other lower alkenyl, Y is independently of the other —COO— or —OCO—, L is independently of the other lower alkylene, $X_1$ is independently of the other —NHCOO— or —OCONH—, p and m are 1; the polymer fragment Q has up to 3 segments (a), up to 4 segments (b) and up to 6 segments (c), wherein in segment (a) the sum of the indices x+y is in the range of 10–15, Z is lower alkylene and k is 0, wherein in segment (b) Alk is lower alkylene, the radicals $R_1$, $R_2$, $R_3$ and $R_4$ are each independently of the others lower alkyl and n is in the range of 14–28, and wherein in segment (c) R is alkylene or arylene having up to 14 carbon atoms or a saturated divalent cycloaliphatic group having 6–14 carbon atoms, and $X_2$ is —NHCOO— or —OCONH—, (2) 15–30% of a hydrophobic monomer, and (3) 10–35% of a hydrophilic monomer, wherein the surface of said moulding is plasma treated in the presence of a $C_1$–$C_4$alkane and air.

Another preferred embodiment relates to a moulding which comprises the polymer of a polymerization product of the following components in weight percent based on the total weight of the polymer:

(1) 45–65% of a macromer according to formula (I) wherein $P_1$ is independently of the other lower alkenyl having up to 4 C-atoms, Y is independently of the other —COO— or —OCO—, L is independently of the other lower alkylene having up to 4 carbon atoms, $X_1$ is independently of the other —NHCOO— or —OCONH—, p and m are 1; the polymer fragment Q has one segment (a), up to 2 segments (b) and up to 2 segments (c), wherein in segment (a) the sum of the indices x+y is in the range of 10–15, Z is lower alkylene and k is 0, wherein in segment (b) Alk is lower alkylene having up to 4 carbon atoms, the radicals $R_1$, $R_2$, $R_3$ and $R_4$ are each independently of the others lower alkyl having up to 4 carbon atoms and n is in the range of 14–28, and wherein in segment (c) R is a saturated divalent cycloaliphatic group having 6–14 carbon atoms, and $X_2$ is —NHCOO— or —OCONH—, (2) 15–30% of a hydrophobic monomer, and (3) 10–35% of a hydrophilic monomer, wherein the surface of said moulding is plasma treated in the presence of a $C_1$–$C_4$alkane and air.

Another preferred embodiment relates to a moulding which comprises the polymer of a polymerization product of the following components in weight percent based on the total weight of the polymer:

(1) 50–60% of a macromer of formula (I) according to the definition in the main claim, wherein $P_1$ is independently of the other lower alkenyl, Y is independently of the other —COO— or —OCO—, L is independently of the other lower alkylene, $X_1$ is independently of the other —NHCOO— or —OCONH—, p and m are 1; the polymer fragment Q has up to 3 segments (a), up to 4 segments (b) and up to 6 segments (c), wherein in segment (a) the sum of the indices x+y is in the range of 10–15, Z is lower alkylene and k is 0, wherein in segment (b) Alk is lower alkylene, the radicals $R_1$, $R_2$, $R_3$ and $R_4$ are each independently of the others lower alkyl and n is in the range of 14–28, and wherein in segment (c) R is alkylene or arylene having up to 14 carbon atoms or a saturated divalent cycloaliphatic group having 6–14 carbon atoms, and $X_2$ is —NHCOO— or —OCONH—, (2) 20–25% of a hydrophobic monomer, and (3) 15–30% of a hydrophilic monomer, wherein the surface of said moulding is plasma treated in the presence of a $C_1$–$C_4$alkane and air.

A more preferred embodiment relates to a moulding which comprises the polymer of a polymerization product of the following components in weight percent based on the total weight of the polymer:

(1) 45–65% of a macromer according to formula (I) wherein $P_1$ is independently of the other lower alkenyl, Y is independently of the other —COO— or —OCO—, L is independently of the other lower alkylene, $X_1$ is independently of the other —NHCOO— or —OCONH—, p and m are 1; the polymer fragment Q has up to 3 segments (a), up to 4 segments (b) and up to 6 segments (c), wherein in segment (a) the sum of the indices x+y is in the range of 10–15, Z is lower alkylene and k is 0, wherein in segment (b) Alk is lower alkylene, the radicals $R_1$, $R_2$, $R_3$ and $R_4$ are each independently of the others lower alkyl and n is in the range of 14–28, and wherein in segment (c) R is alkylene or arylene having up to 14 carbon atoms or a saturated divalent cycloaliphatic group having 6–14 carbon atoms, and $X_2$ is —NHCOO— or —OCONH—, (2) 15–30% of a hydrophobic monomer, and (3) 10–35% of a hydrophilic monomer, wherein the surface of said moulding is plasma treated in the presence of a methane and air.

Another more preferred embodiment relates to a moulding which comprises the polymer of a polymerization product of the following components in weight percent based on the total weight of the polymer:

(1) 45–65% of a macromer according to formula (I) wherein $P_1$ is independently of the other lower alkenyl having up to 4 C-atoms, Y is independently of the other —COO— or —OCO—, L is independently of the other lower alkylene having up to 4 carbon atoms, $X_1$ is independently of the other —NHCOO— or —OCONH—, p and m are 1; the polymer fragment Q has one segment (a), up to 2 segments (b) and up to 2 segments (c), wherein in segment (a) the sum of the indices x+y is in the range of 10–15, Z is lower alkylene and k is 0, wherein in segment (b) Alk is lower alkylene having up to 4 carbon atoms, the radicals $R_1$, $R_2$, $R_3$ and $R_4$ are each independently of the others lower alkyl having up to 4 carbon atoms and n is in the range of 14–28, and wherein in segment (c) R is a saturated divalent cycloaliphatic group having 6–14 carbon atoms, and $X_2$ is —NHCOO— or —OCONH—, (2) 15–30% of a hydrophobic monomer, and (3) 10–35% of a hydrophilic monomer, wherein the surface of said moulding is plasma treated in the presence of a methane and air.

Another more preferred embodiment relates to a moulding which comprises the polymer of a polymerization product of the following components in weight percent based on the total weight of the polymer:

(1) 50–60% of a macromer of formula (I) according to the definition in the main claim, wherein $P_1$ is independently of the other lower alkenyl, Y is independently of the other —COO— or —OCO—, L is independently of the other lower alkylene, $X_1$ is independently of the other —NHCOO— or —OCONH—, p and m are 1; the polymer fragment Q has up to 3 segments (a), up to 4 segments (b) and up to 6 segments (c), wherein in segment (a) the sum of the indices x+y is in the range of 10–15, Z is lower alkylene and k is 0, wherein in segment (b) Alk is lower alkylene, the radicals $R_1$, $R_2$, $R_3$ and $R_4$ are each independently of the others lower alkyl and n is in the range of 14–28, and wherein in segment (c) R is alkylene or arylene having up to 14 carbon atoms or a saturated divalent cycloaliphatic group having 6–14 carbon atoms, and $X_2$ is —NHCOO— or —OCONH—, (2) 20–25% of a hydrophobic monomer, and (3) 15–30% of a hydrophilic monomer, wherein the surface of said moulding is plasma treated in the presence of a methane and air.

The present invention furthermore relates to contact lenses essentially comprising one of the novel polymers or crosslinked polymers, these being high-water-content and soft contact lenses.

The invention furthermore relates to contact lenses essentially comprising one of the novel polymers or crosslinked polymers, these being low-water-content, flexible, gas-permeable (RGP) contact lenses.

Low-water-content contact lenses have usually a water content which is up to 10 percent by weight of water, based on the total weight of a lens.

Accordingly high-water-content contact lenses have usually a water content which exeeds 10 percent by weight.

All the abovementioned advantages naturally apply not only to contact lenses, but also to other novel mouldings.

The present invention furthermore relates to the use of a novel macromer of the formula (I) or a polymer or crosslinked polymer prepared therefrom and described above, for the coating of a base material, for example glass, ceramic or metal, and preferably of polymer substrates, for example ophthalmically usable products such as contact lenses, intraocular lenses or eye bandages, and of medically usable products, for example in surgical or pharmaceutical systems, preference being given in the latter cases (ophthalmic uses) to hydrophilic coatings.

The novel polymers are also suitable for use as corneal implants or artificial corneas and furthermore as cell-growth substrates, as materials for fixing and cultivating animal cells in vitro and in vivo, as medical implants, for example implantable semipermeable membrane materials, as tissue implants for cosmetic surgery, as implants containing hormone-releasing cells, for example islet of Langerhans cells, as breast implants or as artificial joints and the like.

The invention therefore furthermore relates to a corneal implant produced from a polymer as described above. A corneal implant of this type can be produced using the same process as described above for the production of contact lenses. Corneal implants can be implanted using conventional surgical methods, for example under, in or through the epithelial tissue of the cornea or into the stroma of the cornea or into other tissue layers of the cornea. Such implants can modify the optical properties of the cornea, for example in the sense of correcting a visual defect and/or by modifying the appearance of the eye, for example the pupillary coloration. A corneal implant can cover the area over the optical axis which covers the pupil on implantation and provides the ability to see, and furthermore the area surrounding the periphery of the optical axis. The implant can have the same visual properties over the entire area.

It has been found that the flow of high-molecular-weight components of tissue fluid, for example proteins or glycoproteins, e.g. growth factors, peptides, hormones or proteins which are responsible for transport of essential metal ions through the corneal implant, in particular between epithelial cells and stroma cells and even behind the endothelium is important both for survival of tissue and for the ability of tissue to live outside and inside a corneal implant. A corneal implant is therefore preferably produced with a porosity sufficient to allow liquid components of tissue having a molecular weight of >10,000 daltons to pass through, where flow of components of tissue fluid is ensured in addition to flow of low-molecular-weight nutrient components, for example glucose, fats or amino acids or breathing gases between cells on both sides of an implant.

The porosity of a corneal implant is either given by the polymer material from which it is produced or pores can additionally be introduced into a novel polymer by one of the numerous known processes, which are described, for example, in WO 90/07 575, WO 91/07 687, U.S. Pat. No. 5,244,799, U.S. Pat. No. 5,238,613, U.S. Pat. No. 4,799,931 and U.S. Pat. No. 5,213,721.

Irrespective of which method is used to form the requisite porosity of a novel implant, an implant preferably has a porosity sufficient to allow proteins and other biological macromolecules having a molecular weight of up to or greater than 10,000 daltons to pass through, for example a molecular weight of 10,000–1,000,000 daltons, but not so large that entire cells can pass through and penetrate into the area over the optical axis of the implant. Where the porosity of the implant is established by pores, the area over the optical axis contains a multiplicity of pores, whose number is not restricted, but should be sufficient to enable free flow of tissue components between the outer and inner region of an implant. The pores over the area of the optical axis preferably do not cause scattering of visible light to an extent which would cause problems with respect to visual correction. The term pore used above and below is taken to mean a pore which has no geometrical restrictions and has either a regular or irregular morphology. The statement of a pore size does not mean that all the pores have the same diameter, but should be taken as a mean diameter.

In the area outside the optical axis, the corneal implant can have the same porosity as in the area over the optical axis. This peripheral area of an implant, which surrounds the area of the optical axis, is also referred to as the skirt. In contrast to the region of the optical axis, it can allow corneal cells to grow in, anchoring the implant on the eye.

The porosity in the skirt can also be an independent feature of the material from which the skirt is produced. If the skirt is made from the same material as the material over the optical axis, pores having different diameters can be introduced on the one hand in the skirt and on the other hand over the optical axis. On the other hand, the skirt can be produced from another material than the material over the optical axis, in which case, as stated above, the porosity in the skirt should be greater than that over the optical axis. The skirt preferably comprises an optically clear polymer like one over the optical axis; however, the skirt can also comprise a material which is not optically clear or be produced from a porous material which is not optically clear.

A novel polymer can support colonization with tissue cells, for example vascular endothelial cells, fibroblasts or cells formed in bones; it is not necessary for a specific surface nature to be present to stimulate cell adhesion and cell growth. This is advantageous, since the process costs can be kept low. On the other hand, a novel polymer can be surface-modified by known methods, for example plasma treatment of a surface by radio frequency glow discharge, as described, for example, in U.S. Pat. No. 4,919,659 and WO 89/00 220, or by irradiation or by chemical treatment.

A novel polymer can be coated on its surface with one or more components in order, for example, to promote growth of tissue. Examples of such materials are fibronectin, chondroitin sulfate, collagen, laminin, cell attachment proteins, cold insoluble globulin, chondronectin, epidermal growth factors, muscle fibre proteins, and/or derivatives, active fragments and mixtures thereof. Fibronectin, epidermal growth factors and/or derivatives, active fragments and mixtures thereof are particularly useful. A surface coating of this type can, if necessary, also be carried out after a surface modification as described above. A novel polymer can advantageously combine a plurality of said properties, for example the attachment of cells with good biostability and resistance to deposits.

The mechanical properties of a novel polymer are suitable for use as a corneal implant, the material preferably having a modulus of 0.5–10 MPa. A modulus in said range gives a corneal implant a suitable flexibility to enable insertion into the eye, for example over the region of the Bowman membrane.

A novel polymer can furthermore be used as a cell-growth substrate, for example as cell-culture equipment, for example utensils, bottles, dishes and the like, furthermore in biological reactors, for example in the production of valuable proteins and other cell-culture components.

The examples below serve to further illustrate the present invention but are not intended to restrict its scope in any way. Temperatures are given in degrees Celsius.

EXAMPLE A1
Macromer synthesis 51.5 g (50 mmol) of the perfluoropolyether Fomblin® ZDOL (from Ausimont S.p.A, Milan) having a mean molecular weight of 1030 g/mol and containing 1.96 meq/g of hydroxyl groups according to end-group titration is introduced into a three-neck flask together with 50 mg of dibutyltin dilaurate. The flask contents are evacuated to about 20 mbar with stirring and subsequently decompressed with argon. This operation is repeated twice. 22.2 g (0.1 mol) of freshly distilled isophorone diisocyanate kept under argon are subsequently added in a counterstream of argon. The temperature in the flask is kept below 30° C. by cooling with a waterbath. After stirring overnight at room temperature, the reaction is complete. Isocyanate titration gives an NCO content of 1.40 meq/g (theory: 1.35 meq/g).

202 g of the α,ω-hydroxypropyl-terminated polydimethylsiloxane KF-6001 from Shin-Etsu having a mean molecular weight of 2000 g/mol (1.00 meq/g of hydroxyl groups according to titration) are introduced into a flask. The flask contents are evacuated to approx. 0.1 mbar and decompressed with argon. This operation is repeated twice. The degassed siloxane is dissolved in 202 ml of freshly distilled toluene kept under argon, and 100 mg of dibutyltin dilaurate (DBTDL) are added. After complete homogenization of the solution, all the perfluoropolyether reacted with isophorone diisocyanate (IPDI) is added under argon. After stirring overnight at room temperature, the reaction is complete. The solvent is stripped off under a high vacuum at room temperature. Microtitration shows 0.36 meq/g of hydroxyl groups (theory 0.37 meq/g).

13.78 g (88.9 mmol) of 2-isocyanatoethyl methacrylate (IEM) are added under argon to 247 g of the α,ω-hydroxypropyl-terminated polysiloxane-perfluoropolyether-polysiloxane three-block copolymer (a three-block copolymer on stoichiometric average, but other block lengths are also present). The mixture is stirred at room temperature for three days. Microtitration then no longer shows any isocyanate groups (detection limit 0.01 meq/g). 0.34 meq/g of methacryl groups are found (theory 0.34 meq/g).

The macromer prepared in this way is completely colourless and clear. It can be stored in air at room temperature for several months in the absence of light without any change in molecular weight.

EXAMPLE A2
Macromer synthesis

The first step of the macromer synthesis described under Example A1 is repeated. An isocyanate titration of the perfluoropolyether reacted with IPDI gives a content of 1.33 meq/g of NCO (theory 1.35 meq/g).

In a second step, 87.1 g of the α,ω-hydroxypropyl-terminated polydimethylsiloxane Tegomer H-Si 2111 (Th. Goldschmidt AG, Essen) having a mean molecular weight of 890 g/mol (2.25 meq/g of hydroxyl groups according to titration) are dissolved in 87 ml of toluene. After the reaction has been carried out as indicated under A1 and the solvent has been removed, a hydroxyl group content of 0.66 meq/g is determined by microtitration (theory 0.60 meq/g). The resultant intermediate is in turn reacted with a stoichiometric amount of isocyanatoethyl methacrylate. Microtitration then no longer shows any isocyanate groups (detection limit 0.01 meq/g). 0.56 meq/g of methacryl groups are found (theory 0.53 meq/g). The macromer prepared in this way is completely colourless and clear and has a long shelf life.

EXAMPLE A3
Macromer synthesis

The first step of the macromer synthesis described under Example A1 is repeated, but using a different perfluoropolyether: Fomblin® ZDOL TX (from Ausimont S.p.A., Milan). This material is terminated by —O—$CF_2$—$CH_2$—($OCH_2CH_2$)$_n$—OH (n=0, 1 or 2). The material used has a mean molecular weight of 1146 g/mol, and contains 1.72 meq/g of hydroxyl groups according to end-group analysis. An isocyanate titration of the perfluoropolyether reacted with IPDI shows a content of 1.23 meq/g of NCO (theory 1.25 meq/g).

In the second step, a stoichiometric amount of Tegomer Hi-Si 2111 and toluene are again added. After the reaction has been carried out as indicated under Example A1 and the solvent has been removed, a hydroxyl group content of 0.63 meq/g is determined by microtitration (theory 0.58 meq/g). The resultant intermediate is in turn reacted with a stoichiometric amount of isocyanatoethyl methacrylate. Microtitration then no longer shows any isocyanate groups (detection limit 0.01 meq/g). 0.55 meq/g of methacryl groups are found (theory 0.51 meq/g). The macromer prepared in this way is completely colourless and clear and has a long shelf life.

EXAMPLE A4
Macromer synthesis

The first step of the macromer synthesis described under Example A1 is repeated, but 5.0 g of Fomblin® ZDOL and 2.18 g of IPDI are employed. When the reaction is complete, microtitration shows an isocyanate group content of 1.31 meq/g of hydroxyl groups (theory 1.36 meq/g).

The second step of the synthesis described under Example A1 is likewise carried out analogously, the stoichiometric ratio between isocyanate-terminated perfluoropolyether and hydroxypropyl-terminated polysiloxane being 2:3. After the reaction has been completed and the solvent has been removed, microtitration shows a content of 0.2 meq/g of hydroxyl groups (theory 0.18 meq/g).

The third step of the synthesis described under Example A1 is likewise carried out analogously, IEM being employed in a precisely stoichiometric ratio. After the reaction, free isocyanate groups can no longer be detected (detection limit 0.01 meq/g). 0.19 meq/g of methacryl groups are found (theory 0.19 meq/g).

EXAMPLE B1

Production of contact lenses 13.0 g of macromer from Example A1 are dissolved in 5.6 g of ethanol (Fluka, puriss. p.a.) (70% by weight solution). After complete homogenization of the solution, 5.2 g of 3-tris(trimethylsiloxy)silylpropyl methacrylate (TRIS from Shin-Etsu, product No. KF-2801), 7.8 g of freshly distilled dimethylacrylamide (DMA) and 160 mg of photoinitiator Darocur® 1173 (Ciba) are added. This solution is filtered through a Teflon membrane having a pore width of 0.45 mm under an argon pressure of from 1 to 2 atm. The filtered solution is frozen in a flask in liquid nitrogen, the flask is evacuated under a high vacuum, and the solution is returned to room temperature with the flask sealed. This degassing operation is repeated twice. The flask containing the macromer/comonomer solution is then transferred into a glove box with an inert-gas atmosphere, where the solution is pipetted into dust-free contact-lens moulds made from polypropylene. The moulds are closed, and the polymerization reaction is effected by UV irradiation (15 mW/cm$^2$, 5 min.), with simultaneous crosslinking. The moulds are then opened and placed in ethanol, causing the resultant lenses to swell out of the moulds. The lenses are extracted for 24 hours with constantly replenished distilled dichloromethane and subsequently dried in a high vacuum. The dried lenses are equilibrated in phosphate-buffered physiological saline solution in autoclave-resistant vials and then autoclaved at 120° C. for 30 minutes. All physical data measurements are carried out on autoclaved lenses.

The lenses produced in this way are characterized by the following values: oxygen permeability (O$_2$Dk) 77 barrer (determined by the "wet" method described below), water content of the equilibrated lenses 32 percent by weight, elongation at break at 35° C. 360%, modulus of elasticity 30° C. 0.5 MPa (measured using a Minimat from Polymer Laboratories, UK).

"Wet" measurement of the oxygen permeability:

The oxygen permeability of a material is determined by the coulometric method. To this end, pre-autoclaved lenses are clamped in a holder and then covered on the upper side with a 2 cm layer of water. A gas mixture comprising 21% of oxygen and 79% of nitrogen is passed continuously through the water layer with swirling. The oxygen which diffuses through the lens is measured using a coulometric detector. The reference values are those measured on commercially available contact lenses using this method.

Cibasoft® (CIBA-Vision, HEMA lens) gives a measurement of approx. 7–10 barrer, and Excelens® (CIBA-Vision, PVA lens) gives a measurement of approx. 22 barrer.

Unfortunately, the oxygen permeability of, for example, contact lenses is frequently given in the literature as a straight Dk value without further definition and frequently without giving any reference material. These are usually values determined on dry material (dry measurement).

A comparative measurement of the oxygen permeability of polymer B1 shows the differences:

| | |
|---|---|
| a) "wet" measurement | 77 barrer |
| b) dry measurement | 158 barrer |

EXAMPLE B2

The process described under Example B1 for the production of contact lenses is repeated, but the mixture of conomoners has the following composition (in percent by weight):

55% of macromer from Example A1
22% of TRIS
22.5% of DMA
0.5% of Blemer® QA

EXAMPLE B3

The process described under Example B1 for the production of contact lenses is repeated, but the mixture of conomoners has the following composition (in percent by weight):

55% of macromer from Example A1
22% of TRIS
23% of DMA

EXAMPLE B4

Analogously to Example B1 (in percent by weight):
40% of macromer from Example A1
30% of TRIS
30% of DMA

EXAMPLE B5

Analogously to Example B1 (in percent by weight):
30% of macromer from Example A1
45% of TRIS
25% of DMA

EXAMPLE B6

Analogously to Example B1 (in percent by weight):
40% of macromer from Example A1
30% of TRIS
30% of DMAEMA

EXAMPLE B7

Analogously to Example B1 (in percent by weight):
40% of macromer from Example A1
30% of TRIS
30% of NVP

EXAMPLE B8

The process described under B1 for the production of contact lenses is repeated, but a 60% by weight solution of the macromer in ethanol is used instead of the 75% by weight solution described above. The mixture of comonomers has the following composition (in percent by weight):

70% of macromer from Example A2
20% of TRIS
10% of DMA

EXAMPLE B9

Analogously to Example B8 (in percent by weight):
65% of macromer from Example A2

20% of TRIS
15% of DMA

EXAMPLE B10

The process described under B1 for the production of contact lenses is repeated, but a 66% by weight solution of the macromer from Example A2 in ethanol is prepared and, without addition of comonomers, polymerized and crosslinked by UV irradiation after addition of the photoinitiator.

EXAMPLE B11

The process described under B1 for the production of contact lenses is repeated, but a 66% by weight solution of the macromer from Example A3 in ethanol is prepared and, without addition of comonomers, polymerized and crosslinked by UV irradiation after addition of the photoinitiator.

EXAMPLE B12

The process described under B1 for the production of contact lenses is repeated, but a 70% by weight solution of the macromer in toluene is used instead of the 75% by weight solution in ethanol described above. The mixture of comonomers has the following composition (in percent by weight):

55% of macromer from Example A1
22% of TRIS
23% of DMA

EXAMPLE B13

The process described under B1 for the production of contact lenses is repeated, but a 70% by weight solution of the macromer in octamethylcyclotetrasiloxane is used instead of the 75% by weight solution in ethanol described above. The mixture of comonomers has the following composition (in percent by weight):

55% of macromer from Example A1
22% of TRIS
23% of DMA

Physical measurement data for the contact-lens materials from Examples B1 to B13 ($O_2Dk$ value, wet method):

| Example number | Water content [%] | $O_2Dk$ value [barrer] | Modulus of elasticity [MPa] | Elongation at break [%] |
|---|---|---|---|---|
| B1 | 32 | 77 | 0.5 | 360 |
| B2 | 23.8 | 110 | 1.1 | 160 |
| B3 | 19.5 | 110 | 0.6 | 130 |
| B4 | 30.9 | 81 | 0.3 | 300 |
| B5 | 17.1 | — | — | — |
| B6 | 14.4 | — | — | — |
| B7 | 2.3 | — | — | — |
| B8 | 1.8 | 93 | 1.15 | 190 |
| B9 | 5.3 | 88 | 1.25 | 90 |
| B10 | 1.6 | — | — | — |
| B11 | 0.7 | — | — | — |
| B12 | 30 | | | |
| B13 | 25 | | | |

EXAMPLE B14

About 10 g of macromer from Example A1 are dissolved in 3.3 g of ethanol (Fluka, puriss. p.a.). After complete homogenization of the solution, about 4.0 g of 3-tris (trimethylsiloxy)silylpropyl methacrylate (TRIS from Shin-Etsu, product No. KF-2801), about 5.9 g of freshly distilled dimethylacrylamide (DMA), about 0.1 g Blemer® QA (a methacrylate having quaternary substituents, from Linz Chemie) and about 100 mg of photoinitiator Darocur® 1173 (Ciba) are added. This solution is filtered through a Teflon membrane having a pore width of 0.45 mm under an argon pressure of from 1 to 2 atm.

The filtered solution is frozen in a flask in liquid nitrogen, the flask is evacuated under a high vacuum, and the solution is returned to room temperature with the flask sealed. This degassing operation is repeated twice. The flask containing the macromer/comonomer solution is then transferred into a glove box with an inert-gas atmosphere, where the solution is pipetted into dust-free contact-lens moulds made from polypropylene. The moulds are closed, and the polymerization reaction is effected by UV irradiation, with simultaneous crosslinking. The moulds are then opened and placed in isopropanol, causing the resultant lenses to swell out of the moulds. The lenses are extracted for 24 hours with constantly replenished isopropanol and subsequently dried in a high vacuum.

The dried lenses are equilibrated in phosphate-buffered physiological saline solution in autoclave-resistant vials and then autoclaved at 120° C. for 30 minutes. All physical data measurements are carried out on autoclaved lenses.

| Water content [%] | $O_2Dk$ value [barrer] | Modulus of elasticity [MPa] |
|---|---|---|
| 20.3 | 93 | 0.96 |

EXAMPLE B15

Lenses are prepared in accordance with the procedures described in example B14, but are subsequently surface treated as follows. The dried lenses are transferred into a plasma coating apparatus wherein they are plasma treated in a methane/"air" mixture ("air" as used here denotes 79% nitrogen and 21% oxygen) for a period of about 5 minutes. The apparatus and plasma treatment process have been disclosed by H. Yasuda in "Plasma Polymerization", Academic Press, Orlando, Fla. (1985), pages 319 forward.

The plasma treated contact lenses are equilibrated in phosphate-buffered physiological saline solution in autoclave-resistant vials and then autoclaved at 120° C. for 30 minutes. All physical data measurements are carried out on autoclaved lenses.

| Water content [%] | $O_2Dk$ value [barrer] | Modulus of elasticity [MPa] |
|---|---|---|
| 21.8 | 88 | 1.03 |

EXAMPLE B16

Lenses are prepared in accordance to example B1, but the mixture of the comonomers has the following composition in weight percentages:

60% of macromer from Example A1
25% of TRIS
15% of DMA

EXAMPLE B17

Lenses are prepared in accordance to example B1, but the mixture of the comonomers has the following composition in weight percentages:

50% of macromer from Example A1
20% of TRIS
30% of DMA

The lenses are equilibrated in phosphate-buffered physiological saline solution in autoclave-resistant vials and then autoclaved at 120° C. for 30 minutes. All physical data measurements are carried out on autoclaved lenses.

| Water content [%] | O$_2$Dk value [barrer] | Elongation at break [%] |
|---|---|---|
| 24 | 78 | 300 |

EXAMPLE B18

The lenses of example B17 are plasma treated in analogy to the lenses of example B15.

The plasma treated lenses are then equilibrated in phosphate-buffered physiological saline solution in autoclave-resistant vials and then autoclaved at 120° C. for 30 minutes. All physical data measurements are carried out on autoclaved lenses.

| Water content [%] | O$_2$Dk value [barrer] | Modulus of elasticity [MPa] |
|---|---|---|
| 21.5 | 95 | 1.1 |

What is claimed is:

1. A macromer of the formula (I)

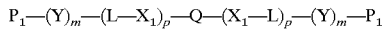

$$P_1-(Y)_m-(L-X_1)_p-Q-(X_1-L)_p-(Y)_m-P_1 \quad (I)$$

where each $P_1$, independently of the others, is a free-radical-polymerizable group; each Y, independently of the others, is —CONHCOO—, —CONHCONH—, —OCONHCO—, —NHCONHCO—, —NHCO—, —CONH—, —NHCONH—, —COO—, —OCO—, —NHCOO— or —OCONH—; m and p, independently of one another, are 0 or 1; each L, independently of the others, is a divalent radical of an organic compound having up to 20 carbon atoms; each $X_1$, independently of the others, is —NHCO—, —CONH—, —NHCONH—, —COO—, —OCO—, —NHCOO— or —OCONH—; and Q is a bivalent polymer fragment consisting of the segments (a) —(E)$_k$—Z—CF$_2$—(OCF$_2$)$_x$—(OCF$_2$CF$_2$)$_y$—OCF$_2$—Z—(E)$_k$—, where x+y is a number in the range from 10 to 30; each Z, independently of the others, is a divalent radical having up to 12 carbon atoms or a bond; each E, independently of the others, is —(OCH$_2$CH$_2$)$_q$, where q has a value of from 0 to 2, and where the link —Z—E— represents the sequence —Z—(OCH$_2$CH$_2$)$_q$—; and k is 0 or 1;

(b)

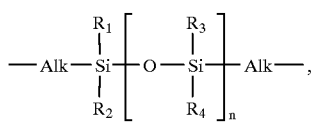

where n is an integer from 5 to 100; Alk is alkylene having up to 20 carbon atoms; 80–100% of the radicals $R_1$, $R_2$, $R_3$ and $R_4$, independently of one another, are alkyl and 0–20% of the radicals $R_1$, $R_2$, $R_3$ and $R_4$, independently of one another, are alkenyl, aryl or cyanoalkyl; and (c) $X_2$—R—$X_2$, where R is a divalent organic radical having up to 20 carbon atoms, and each $X_2$, independently of the others, is —NHCO—, —CONH—, —NHCONH—, —COO—, —OCO—, —NHCOO— or —OCONH—;

with the proviso that each segment (a) or (b) has a segment (c) attached to it; and each segment (c) has a segment (a) or (b) attached to it.

2. A macromer according to claim 1, in which the number of segments (b) in the polymer fragment Q is greater than or equal to the number of segments (a).

3. A macromer according to claim 1, in which the ratio between segments (a) and (b) in polymer fragment Q is 3:4, 2:3, 1:2 or 1:1.

4. A macromer according to claim 1, in which the mean molecular weight of the polymer fragment Q is in the range from about 1000 to about 20000.

5. A macromer according to claim 1, in which the total number of segments (a) and (b) in the polymer fragment Q is in the range from 2 to about 11.

6. A macromer according to claim 1, in which the smallest polymer fragment Q comprises, on stoichiometric average, one perfluoro segment (a), one siloxane segment (b) and one segment (c).

7. A macromer according to claim 1, in which the polymer fragment Q is terminated, on stoichiometric average, at each end by a siloxane segment (b).

8. A macromer according to claim 1, in which $X_1$ is —NHCONH—, —NHCOO— or —OCONH—.

9. A macromer according to claim 1, in which the segment $X_2$—R—$X_2$ is a radical derived from a diisocyanate, where each $X_2$, independently of the other, is —NHCONH—, —NHCOO or —OCONH—.

10. A macromer according to claim 1, in which Z is a bond, lower alkylene or —CONH-arylene, where the —CO— moiety is linked to a CF$_2$ group.

11. A macromer according to claim 1, in which Z is lower alkylene.

12. A macromer according to claim 1, in which the indices x+y are a number in the range from 10 to 25.

13. A macromer according to claim 1, in which the ratio x:y is in the range from 0.5 to 1.5.

14. A macromer according to claim 1, in which the free-radical-polymerizable group $P_1$ is alkenyl, alkenylaryl or alkenylarylenealkyl having up to 20 carbon atoms.

15. A macromer according to claim 1, in which $P_1$ is alkenyl or alkenylaryl having up to 12 carbon atoms.

16. A macromer according to claim 1, in which Y is —COO—, —OCO—, —NHCONH—, —NHCOO—, —OCONH—, —NHCO— or —CONH—.

17. A macromer according to claim 1, in which the indices m and p are not simultaneously zero.

18. A macromer according to claim 1, in which L is alkylene, arylene, aiylenealkylene, alkylenearylene, alkylenearylenealkene or arylenealkylenearylene.

19. A macromer according to claim 1, in which L is alkylene or arylene having up to 12 carbon atoms.

20. A macromer according to claim 1, in which the divalent radical R is alkylene, arylene, alkylenearylene, arylenealkylene or arylenealkylenearylene having up to 20 carbon atoms or cycloalkylenealkylenecycloalkylene having 7 to 20 carbon atoms.

21. A macromer according to claim 1, in which R is alkylene, arylene, alkylenearylene, arylenealkylene or arylenealkylenearylene having up to 14 carbon atoms.

22. A macromer according to claim 1, in which R is alkylene, arylene, alkylenearylene or arylenealkylene having up to 14 carbon atoms.

23. A macromer according to claim 1, in which n is an integer from 5 to 70.

24. A macromer according to claim 1, in which 85–100% of the radicals $R_1$, $R_2$, $R_3$ and $R_4$, independently of one another, are lower alkyl having up to 8 carbon atoms.

25. A macromer according to claim 1, in which 0–15% of the radicals $R_1$, $R_2$, $R_3$ and $R_4$, independently of one another, are lower alkenyl, phenyl which is unsubstituted or substituted by lower alkyl or lower alkoxy, or cyano(lower alkyl).

26. A macromer according to claim 1, wherein $P_1$ is, independently of the other, lower alkenyl, Y is, independently of the other, —COO— or —OCO—, L is independently of the other, lower alkylene, $X_1$ is, independently of the other, —NHCOO— or —OCONH—, p and m are 1; the polymer fragment Q has up to 3 segments (a), up to 4 segments (b) and up to 6 segments (c), wherein in segment (a) the sum of the indices x+y is in the range of 10–15, Z is lower alkylene and k is 0, wherein in segment (b) Alk is lower alkylene, the radicals $R_1$, $R_2$, $R_3$ and $R_4$ are each, independently of the others, lower alkyl and n is in the range of 14–28, and wherein in segment (c) R is alkylene or arylene having up to 14 carbon atoms or a saturated divalent cycloaliphatic group having 6–14 carbon atoms, and $X_2$ is —NHCOO— or —OCONH—.

27. A macromer according to claim 1, wherein $P_1$ is, independently of the other, lower alkenyl, Y is, independently of the other, —COO— or —OCO—, L is, independently of the other, lower alkylene, $X_1$ is, independently of the other, —NHCOO— or —OCONH—, p and m are 1; the polymer fragment Q has a segment (a), up to 2 segments (b) and up to 2 segments (c), wherein in segment (a) the sum of the indices x+y is in the range of 10–15, Z is lower alkylene and k is 0, wherein in segment (b) Alk is lower alkylene, the radicals $R_1$ $R_2$, $R_3$ and $R_4$ are each, independently of the others, lower alkyl and n is in the range of 14–28, and wherein in segment (c) R is alkylene or arylene having up to 14 carbon atoms or a saturated divalent cycloaliphatic group having 6–14 carbon atoms, and $X_2$ is —NHCOO or —OCONH—.

28. A macromer according to claim 1, wherein $P_1$ is, independently of the other, alkenyl having up to 4 carbon atoms, Y is, independently of the other, —COO— or —OCO—, L is —OCONH—, p and m are 1; the polymer fragment Q has a segment (a), 2 segments (b) 2 segments (c), wherein in segment (a) the sum of the indices x+y is in the range of 10–15, Z is lower alkylene and k is 0, wherein in segment (b) Alk is lower alkylene, the radicals $R_1$, $R_2$, $R_3$ and $R_4$ are each, independently of the others, lower alkyl and n is in the range of 14–28, and wherein in segment (c) R is alkylene or arylene having up to 14 carbon atoms or a saturated divalent cycloaliphatic group having 6–14 carbon atoms, and $X_2$ is —NHCOO— or —OCONH—.

29. A macromer according to claim 1, wherein $P_1$ is, independently of the other, lower alkenyl, Y is, independently of the other, —COO— or —OCO—, L is, independently of the other, lower alkylene, $X_1$ is, independently of the other, —NHCOO— or —OCONH—, p and m are 1; the polymer fragment Q has a segment (a), up to 2 segments (b) and up to 2 segments (c), wherein in segment (a) the sum of the indices x+y is in the range of 10–15, Z is lower alkylene and k is 0, wherein in segment (b) Alk is lower alkylene, the radicals $R_1$, $R_2$, $R_3$ and $R_4$ are each methyl and n is in the range of 14–28, and wherein in segment (c) R is alkylene or arylene having up to 14 carbon atoms or a saturated divalent cycloaliphatic group having 6–14 carbon atoms, and $X_2$ is —NHCOO— or —OCONH—.

30. A macromer according to claim 1, wherein $P_1$ is, independently of the other, lower alkenyl having up to 4 C-atoms, Y is, independently of the other, —COO— or —OCO—, L is, independently of the other, lower alkylene having up to 4 carbon atoms, $X_1$ is, independently of the other, —NHCOO— or —OCONH—, p and m are 1; the polymer fragment Q has a segment (a), up to 2 segments (b) and up to 2 segments (c), wherein in segment (a) the sum of the indices x+y is in the range of 10–15, Z is lower alkylene and k is 0, wherein in segment (b) Alk is lower alkylene having up to 4 carbon atoms, the radicals $R_1$, $R_2$, $R_3$ and $R_4$ are each, independently of the others, lower alkyl having up to 4 carbon atoms and n is in the range of 14–28, and wherein in segment (c) R is a saturated divalent cycloaliphatic group having 6–14 carbon atoms, and $X_2$ is —NHCOO— or —OCONH—.

31. A process for the preparation of a macromer according to claim 1, wherein a perfluoropolyalkyl ether derivative of the formula (IV)

$$X_3\text{—(E)}_k\text{—Z—CF}_2\text{—(OCF}_2)_x\text{—(OCF}_2\text{CF}_2)_y\text{—OCF}_2\text{—Z—(E)}_k\text{—}X_3 \quad \text{(IV)}$$

in which $X_3$ is —OH, —NH$_2$, —COOH, —COCl, —NCO or -COOR$_5$, where —COOR$_5$ is an activated ester in which R$_5$ is alkyl or aryl which is unsubstituted or substituted by halogen or cyano, and the variables Z, E, k, x and y are as defined above, is reacted with two equivalents of a bifunctional radical of the formula (V)

$$X_4\text{—R—}X_4 \quad \text{(V)}$$

in which R is as defined above and $X_4$ is a functional radical of —OH—, —NH$_2$, —COOH, —COCl, —COOR$_5$ or —NCO which is coreactive with an $X_3$, in the presence or absence of a suitable catalyst, where the reaction of $X_3$ with $X_4$ gives a Group $X_2$; after which a reactive derivative of the formula (VI)

$$X_4\text{—R—}X_2\text{—(E)}_k\text{—Z—CF}_2\text{—(OCF}_2)x\text{-(OCF}_2\text{CF}_2)_y\text{—OCF}_2\text{-z-}(E)_k\text{—}X_2\text{—R—}X_4 \quad \text{(VI)}$$

is obtained which is then reacted with two equivalents of an α,ω-substituted siloxane of the formula (VII)

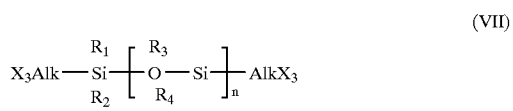

(VII)

where the variables $R_1$, $R_2$, $R_3$, $R_4$, n, $X_3$ and Alk are as defined above, in the presence or absence of a suitable catalyst, giving a compound of the formula (VIII)

$$X_3\text{-Sil-}X_2\text{—R—}X_2\text{—PFPE—}X_2\text{—R—}X_2\text{-Sil-}X_3 \quad \text{(VIII)}$$

in which PFPE is $(E)_k$—Z—CF$_2$—(OCF$_2$),—(OCF$_2$CF$_2$)y-OCF$_2$—Z—$(E)_k$, Sil is the siloxane radical

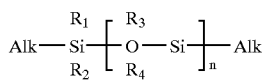

and the other variables are as defined above; after which the reactive intermediate of the formula (VIII) is preferably reacted with two equivalents of a compound of the formula (IXa) or (IXb)

P₁—(Y)ₘ—L—X₄ (IXa)

P₁Y₂ (IXb)

in the presence or absence of a catalyst, to give the macromer of the formula (I)

P₁—(Y)ₘ—(L—X₁)ₚ—Q—(X₁—L)ₚ—(Y)ₘ—P₁ in which Y₂ is a functional radical which is coreactive with X₃ and is —OH, —NH₂, —COOH, —COCl, —COOR₅, —CONCO or —NCO, and the variables are as defined above, and in which X₁ is formed from the reaction of X₃ with X₄ and Y is formed from the reaction of Y₂ with X₃.

32. A polymer comprising a product of the polymerization of at least one compound of the formula (I) as defined in claim 1.

33. A polymer according to claim 32, wherein the proportion by weight of the compound of the formula (I) is in the range from 100 to 0.5%.

34. A polymer according to claim 32, which further comprises a vinylic comonomer (a).

35. A polymer according to claim 34, wherein the comonomer (a) is hydrophilic or hydrophobic or a mixture thereof.

36. A polymer according to claim 32, wherein the comonomer (a) is tristrimethylsilyloxysilylpropyl methacrylate, 2-hydroxyethyl methacrylate, dimethylaminoethyl methacrylate, tiimethylammonium 2-hydroxypropylmethacrylate hydrochloride, N,N-dimethylacrylamide or N-vinyl-2-pyrrolidone.

37. A crosslinked polymer comprising a product of the polymerization of at least one compound of the formula (1) as defined in claim 1 with at least one comonomer selected from the group consisting of a vinylic comonomer (a) and a polyunsaturated comonomer (b).

38. A polymer which comprises the polymerization product of the following components in weight percent based on the total weight of the polymer:
   (1) 45–65% of a macromer according to claim 1,
   (2) 15–30% of a hydrophobic monomer, and
   (3) 10–35% of a hydrophilic monomer.

39. A polymer according to claim 38, comprising:
   (1) 50–60% of a macromer according to claim 1,
   (2) 20–25% of a hydrophobic monomer, and
   (3) 15–30% of a hydrophlic monomer.

40. A polymer according to claim 38, comprising:
   (1) 50–60% of a macromer of formula (1) according to claim 1, wherein P₁ is, independently of the other, lower alkenyl, Y is, independently of the other, —COO— or —OCO—, L is, independently of the other, lower alkylene, X₁ is, independently of the other, —NHCOO— or —OCONH—, p and m are 1; the polymer fragment Q has up to 3 segments (a), up to 4 segments (b) and up to 6 segments (c), wherein in segment (a) the sum of the indices x+y is in the range of 10–15, Z is lower alkylene and k is 0, wherein in segment (b) Alk is lower alkylene, the radicals R₁, R₂, R₃ and R₄ are each independently of the others lower alkyl and n is in the range of 14–28, and wherein in segment (c) R is alkylene or arylene having up to 14 carbon atoms or a saturated divalent cycloaliphatic group having 6–14 carbon atoms, and X₂ is —NHCOO— or —OCONH—,
   (2) 20–25% of a hydrophobic monomer, and
   (3) 15–30% of a hydrophilic monomer.

41. A molding comprising a polymer according to claim 32.

42. A moulding according to claim 41, which is a contact lens.

43. A moulding according to claim 42, which is an intraocular lens.

44. A moulding according to claim 41 wherein the surface of the moulding is plasma treated in the presence of a C₁–C₆alkane (a) and a gas (b) which is selected from the group consisting of nitrogen, argon, oxygen, and mixtures thereof.

45. A moulding which comprises the polymer of a polymerization product of the following components in weight percent based on the total weight of the polymer:
   (1) 45–65% of a macromer according to formula (I) of claim 1 wherein P₁ is, independently of the other, lower alkenyl having up to 4 C-atoms, Y is, independently of the other, —COO— or —OCO—, L is, independently of the other, lower alkylene having up to 4 carbon atoms, X₁ is, independently of the other, —NHCOO— or —OCONH—, p and m are 1; the polymer fragment Q has one segment (a), up to 2 segments (b) and up to 2 segments (c), wherein in segment (a) the sum of the indices x+y is in the range of 10–15, Z is lower alkylene and k is 0, wherein in segment (b) Alk is lower alkylene having up to 4 carbon atoms, the radicals R₁, R₂, R₃ and R₄ are, each independently of the others, lower alkyl having up to 4 carbon atoms and n is in the range of 14–28, and wherein in segment (c) R is a saturated divalent cycloaliphatic group having 6–14 carbon atoms, and X₂ is —NHCOO— or —OCONH—,
   (2) 15–30% of a hydrophobic monomer, and
   (3) 10–35% of a hydrophilic monomer,
wherein the surface of said moulding is plasma treated in the presence of a methane and air.

46. A biomedical article comprising a polymer according to claim 32.

47. A corneal implant comprising a polymer according to claim 32.

48. A corneal implant according to claim 47 which can be used in surgical implantation on or in the cornea of a mammal, where said implant has an optical property in the region over the optical axis which is suitable for impairing visual acuity, furthermore has a porosity which is sufficient to allow components of tissue fluid having a molecular weight of greater than 10,000 daltons to pass through, with flow of tissue fluid from cells outside the implant to cells inside the implant being ensured, and where the porosity in the region over the optical axis is arranged to such an extent that flow of components of tissue fluid is possible, but ingrowth of ocular tissue is excluded.

49. A corneal implant according to claim 47, where the implant is coated with one or more components which promote growth of tissue in the vicinity of the implant and/or promote cell adhesion to the implant.

50. A corneal implant according to claim 47, where the porosity of the implant is provided by a multiplicity of pores whose size is sufficient to ensure flow of protein components of tissue fluid having a molecular weight of more than 10,000 daltons through the implant, but whose pore size excludes ingrowth of tissue.

51. A corneal implant according to claim 49, where the majority of the pores have a diameter of from 15 nanometers to 0.5 microns.

52. A cell-growth substrate comprising a polymer according to claim 32.

53. A medical implant comprising a polymer according to claim 32.

54. A macromer according to claim 4, in which the mean molecular weight of the polymer fragment Q is in the range from about 3000 to about 15,000.

55. A macromer according to claim 54, in which the mean molecular weight of the polymer fragment Q is in the range from about 5000 to about 12,000.

56. A macromer according to claim 5, in which the total number of segments (a) and (b) in the polymer fragment Q is in the range from 2 to about 9.

57. A macromer according to claim 56, in which the total number of segments (a) and (b) in the polymer fragment Q is in the range from 2 to about 7.

58. A macromer according to claim 12, in which the indices x+y are a number in the range from 10 to 15.

59. A macromer according to claim 13, in which the ratio x:y is in the range from 0.7 to 1.1.

60. A macromer according to claim 15, in which $P_1$ is alkenyl or alkenylaryl having up to 8 carbon atoms.

61. A macromer according to claim 60, in which $P_1$ is alkenyl or alkenylaryl having up to 4 carbon atoms.

62. A macromer according to claim 23, in which n is an integer from 10 to 50.

63. A macromer according to claim 62, in which n is an integer from 14 to 28.

64. A macromer according to claim 24, in which 90–100% of the radicals $R_1$ $R_2$, $R_3$ and $R_4$, independently of one another, are lower alkyl having up to 4 carbon atoms.

65. A polymer according to claim 33, wherein the proportion by weight of the compound of the formula (I) is in the range from 80 to 10%.

66. A polymer according to claim 65, wherein the proportion by weight of the compound of the formula (I) is in the range from 70 to 30%.

67. An article having a surface coating which comprises a macromer of formula (I) of claim 1.

68. An article having a surface coating which comprises a polymer of claim 32.

* * * * *